(12) United States Patent
Amit

(10) Patent No.: US 10,631,935 B2
(45) Date of Patent: Apr. 28, 2020

(54) HEAD REGISTRATION USING A PERSONALIZED GRIPPER

(71) Applicant: Biosense Webster (Israel) Ltd., Yokneam (IL)

(72) Inventor: Matityahu Amit, Cohav-Yair-Zur-Yigal (IL)

(73) Assignee: Biosense Webster (Israel) Ltd., Yokneam (IL)

(*) Notice: Subject to any disclaimer, the term of this patent is extended or adjusted under 35 U.S.C. 154(b) by 289 days.

(21) Appl. No.: 15/334,183

(22) Filed: Oct. 25, 2016

(65) Prior Publication Data

US 2018/0110567 A1 Apr. 26, 2018

(51) Int. Cl.
*A61B 34/20* (2016.01)
*B33Y 80/00* (2015.01)
(Continued)

(52) U.S. Cl.
CPC ............ *A61B 34/20* (2016.02); *A61B 5/0555* (2013.01); *A61B 6/04* (2013.01); *A61B 17/24* (2013.01);
(Continued)

(58) Field of Classification Search
CPC ......... A61B 34/20; A61B 34/10; A61B 90/37; A61B 90/39; A61B 5/0555; A61B 5/06;
(Continued)

(56) References Cited

U.S. PATENT DOCUMENTS

| 4,164,943 A * | 8/1979 | Hill | .............. A61M 25/02 128/DIG. 26 |
| 5,391,199 A | 2/1995 | Ben-Haim | |

(Continued)

FOREIGN PATENT DOCUMENTS

| EP | 0951874 A2 | 10/1999 |
| GB | 2382777 | 11/2003 |

(Continued)

OTHER PUBLICATIONS

European Search Report and Written Opinion dated Feb. 26, 2018 for Application No. 17197953.7, 7 pages.

*Primary Examiner* — Amelie R Davis
*Assistant Examiner* — John Denny Li
(74) *Attorney, Agent, or Firm* — Frost Brown Todd LLC

(57) ABSTRACT

A method includes acquiring an anatomical image of at least part of a head of a specific patient, the anatomical image capturing at least a selected location in the head. A personalized gripper, which is shaped based on the anatomical image to personally fit an organ of the specific patient at the selected location, and which includes a first position sensor of a position-tracking system, is fitted. The anatomical image is registered with a coordinate system of the position-tracking system, by identifying the selected location in the anatomical image and measuring a first position of the first position sensor using the position-tracking system. A medical device that includes a second position sensor of the position-tracking system, is navigated in the head of the specific patient by displaying a second position of the medical device in the head on the registered anatomical image.

14 Claims, 3 Drawing Sheets

(51) Int. Cl.
- *A61B 34/10* (2016.01)
- *A61B 17/24* (2006.01)
- *A61B 90/00* (2016.01)
- *A61B 5/055* (2006.01)
- *A61B 6/04* (2006.01)
- *A61B 17/00* (2006.01)

(52) U.S. Cl.
CPC .............. *A61B 34/10* (2016.02); *A61B 90/37* (2016.02); *A61B 90/39* (2016.02); *B33Y 80/00* (2014.12); *A61B 2017/00526* (2013.01); *A61B 2034/102* (2016.02); *A61B 2034/108* (2016.02); *A61B 2034/2051* (2016.02); *A61B 2034/2055* (2016.02); *A61B 2090/374* (2016.02); *A61B 2090/3762* (2016.02); *A61B 2090/3764* (2016.02); *A61B 2090/3991* (2016.02)

(58) Field of Classification Search
CPC ....... A61B 6/04; A61B 17/24; A61B 2034/10; A61B 2034/102; A61B 2034/108; A61B 2034/2051; A61B 2034/2055; A61B 2090/374; A61B 2090/3762; A61B 2090/3764; A61B 2090/3991; A61B 2017/00526; B33Y 80/00
USPC .......................................................... 600/411
See application file for complete search history.

(56) References Cited

U.S. PATENT DOCUMENTS

| | | | |
|---|---|---|---|
| 5,636,255 A | 6/1997 | Ellis | |
| 6,096,048 A * | 8/2000 | Howard, III | ........... A61B 90/10 600/414 |
| 6,239,724 B1 | 5/2001 | Doron et al. | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 7,014,461 B2 | 3/2006 | Weinstein | |
| 7,636,459 B2 | 12/2009 | Dore et al. | |
| 7,747,305 B2 | 6/2010 | Dean et al. | |
| 8,775,133 B2 | 7/2014 | Schroeder | |
| 8,790,408 B2 | 7/2014 | Marotta | |
| 8,984,731 B2 | 3/2015 | Broeck et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2007/0078334 A1* | 4/2007 | Scully | ....................... A61B 5/06 600/424 |
| 2008/0030345 A1* | 2/2008 | Austin | ................... A61B 90/90 340/572.8 |
| 2009/0129556 A1* | 5/2009 | Ahn | ........................ A61B 6/04 378/208 |
| 2009/0267261 A1* | 10/2009 | Mark | ................... A61M 16/06 264/222 |
| 2010/0047752 A1 | 2/2010 | Chan et al. | |
| 2012/0245456 A1* | 9/2012 | Kim | ...................... A61B 1/313 600/424 |
| 2012/0292814 A1 | 11/2012 | Spratt et al. | |
| 2013/0071811 A1 | 3/2013 | Groscurth et al. | |
| 2013/0261783 A1* | 10/2013 | Daon | ..................... G06F 17/50 700/118 |
| 2014/0037174 A1 | 2/2014 | Ernst et al. | |
| 2014/0171784 A1 | 6/2014 | Ooi et al. | |
| 2014/0209095 A1* | 7/2014 | Anca | ................. A61M 16/0488 128/200.26 |
| 2015/0118640 A1 | 4/2015 | Schmitt | |
| 2015/0150684 A1 | 6/2015 | De Clerck | |
| 2015/0196372 A1 | 7/2015 | Champleboux | |
| 2015/0273170 A1 | 10/2015 | Bachelder et al. | |
| 2015/0287247 A1 | 10/2015 | Willis et al. | |
| 2015/0297177 A1 | 10/2015 | Boctor et al. | |
| 2016/0008083 A1* | 1/2016 | Kesten | .................. A61B 5/062 600/424 |
| 2016/0184068 A1* | 6/2016 | Chodorow | ............ A61C 1/084 433/71 |
| 2017/0236272 A1* | 8/2017 | Holsing | ................ A61B 5/061 382/128 |

FOREIGN PATENT DOCUMENTS

| | | |
|---|---|---|
| WO | WO 1996/005768 A1 | 2/1996 |
| WO | WO 2013/144939 A1 | 10/2013 |
| WO | WO 2013/172919 A1 | 11/2013 |
| WO | WO 2015/157703 | 10/2015 |

\* cited by examiner

HEAD REGISTRATION USING A PERSONALIZED GRIPPER

FIELD OF THE INVENTION

The present invention relates generally to invasive medical devices, and particularly to methods and systems for registration of an anatomical image with a position-tracking system.

BACKGROUND OF THE INVENTION

Registration of an anatomical image with a position-tracking system may be carried out in various medical applications.

For example, U.S. Patent Application Publication 2014/0037174, issued as U.S. Pat. No. 9,076,212 on Jul. 7, 2015, whose disclosure is incorporated herein by reference, describes a system that adaptively compensates for subject motion in real-time in an imaging system. An object orientation marker, preferably a retro-grate reflector (RGR), is placed on the head or other body organ of interest of a patient during a scan, such as an MRI scan. The marker makes it possible to measure the six degrees of freedom (x, y, and z-translations, and pitch, yaw, and roll), or "pose", required to track motion of the organ of interest. This invention also provides for internal calibration and for co-registration over time of the scanner's and tracking system's reference frames to compensate for drift and other inaccuracies that may arise over time.

U.S. Pat. No. 7,014,461, whose disclosure is incorporated herein by reference, describes an apparatus for measuring a surface geometry of hard tissue covered by a layer of soft tissue, including a plurality of elements each having a tip adapted to penetrate said soft tissue and not substantially penetrate said hard tissue; a frame supporting movement of said elements, each along a path, such that a plurality of said tips, when positioned along the paths, define a surface; and at least one position sensor which generates a signal indicative of a tip position of at least one of said elements.

U.S. Pat. No. 5,636,255, whose disclosure is incorporated herein by reference, describes method and system for correlating accuracy of computer tomography (CT) image resolution. Small radio-opaque markers having a diameter less than one slice width of a CT scan are embedded in the object, such as a bony skeletal member, to be measured, the object is then CT scanned so that the radio-opaque markers appear in at two slices of the scan. The markers are also physically located by detecting them with a sensor, such as a positioning pointer.

SUMMARY OF THE INVENTION

An embodiment of the present invention that is described herein provides a method including acquiring an anatomical image of at least part of a head of a specific patient. The anatomical image captures at least a selected location in the head. A personalized gripper, which is shaped based on the anatomical image to personally fit an organ of the specific patient at the selected location, and which includes a first position sensor of a position-tracking system, is fitted. The anatomical image is registered with a coordinate system of the position-tracking system, by identifying the selected location in the anatomical image and measuring a first position of the first position sensor using the position-tracking system. A medical device that includes a second position sensor of the position-tracking system, is navigated in the head of the specific patient by displaying a second position of the medical device in the head on the registered anatomical image.

In some embodiments, acquiring the anatomical image includes acquiring one or more images of a modality selected from a list consisting of computerized tomography (CT), cone beam computed tomography (CBCT), and magnetic resonance imaging (MRI). In other embodiments, the selected location includes one or more teeth of the specific patient. In yet other embodiments, the selected location includes at least part of an upper jaw and at least part of a lower jaw of the specific patient, and fitting the personalized gripper includes fitting a bite bar, which is shaped to personally fit the at least part of the upper jaw and the at least part of the lower jaw of the specific patient.

In an embodiment, the selected location includes at least part of a nose of the specific patient. In another embodiment, the selected location includes at least part of a cranium of the specific patient. In yet another embodiment, fitting the personalized gripper includes coupling the first position sensor to the personalized gripper, and subsequently attaching the personalized gripper to the organ.

In some embodiments, the personalized gripper is provided with the first position sensor embedded therein. In other embodiments, navigating the medical device includes navigating the medical device into a nasal-sinus of the head. In yet other embodiments, navigating the medical device includes navigating the medical device into a neural-system of the head.

In an embodiment, the medical device includes a suction catheter. In another embodiment, the medical device includes a guidewire.

In some embodiments, the position-tracking system includes a magnetic position-tracking system, and the first and second position sensors include magnetic position sensors. In other embodiments, the position-tracking system includes an optical position-tracking system, and the first and second position sensors include optical markers.

There is additionally provided, in accordance with an embodiment of the present invention, a method for producing a gripper, including receiving an anatomical image of at least part of a head of a specific patient, wherein the anatomical image captures at least a selected location in the head. Instructions are derived from the anatomical image for producing a personalized gripper that is shaped to personally fit an organ at the selected location. The personalized gripper is produced based on the instructions, and a position sensor is coupled to the personalized gripper.

There is further provided, in accordance with an embodiment of the present invention, an article of manufacture including a personalized gripper body, which is shaped to personally fit an organ at a selected location in a head of a specific patient, based on an anatomical image of at least part of the head of the specific patient, and a position sensor coupled to the personalized gripper body.

The present invention will be more fully understood from the following detailed description of the embodiments thereof, taken together with the drawings in which:

DETAILED DESCRIPTION OF EMBODIMENTS

Overview

Figure 1:
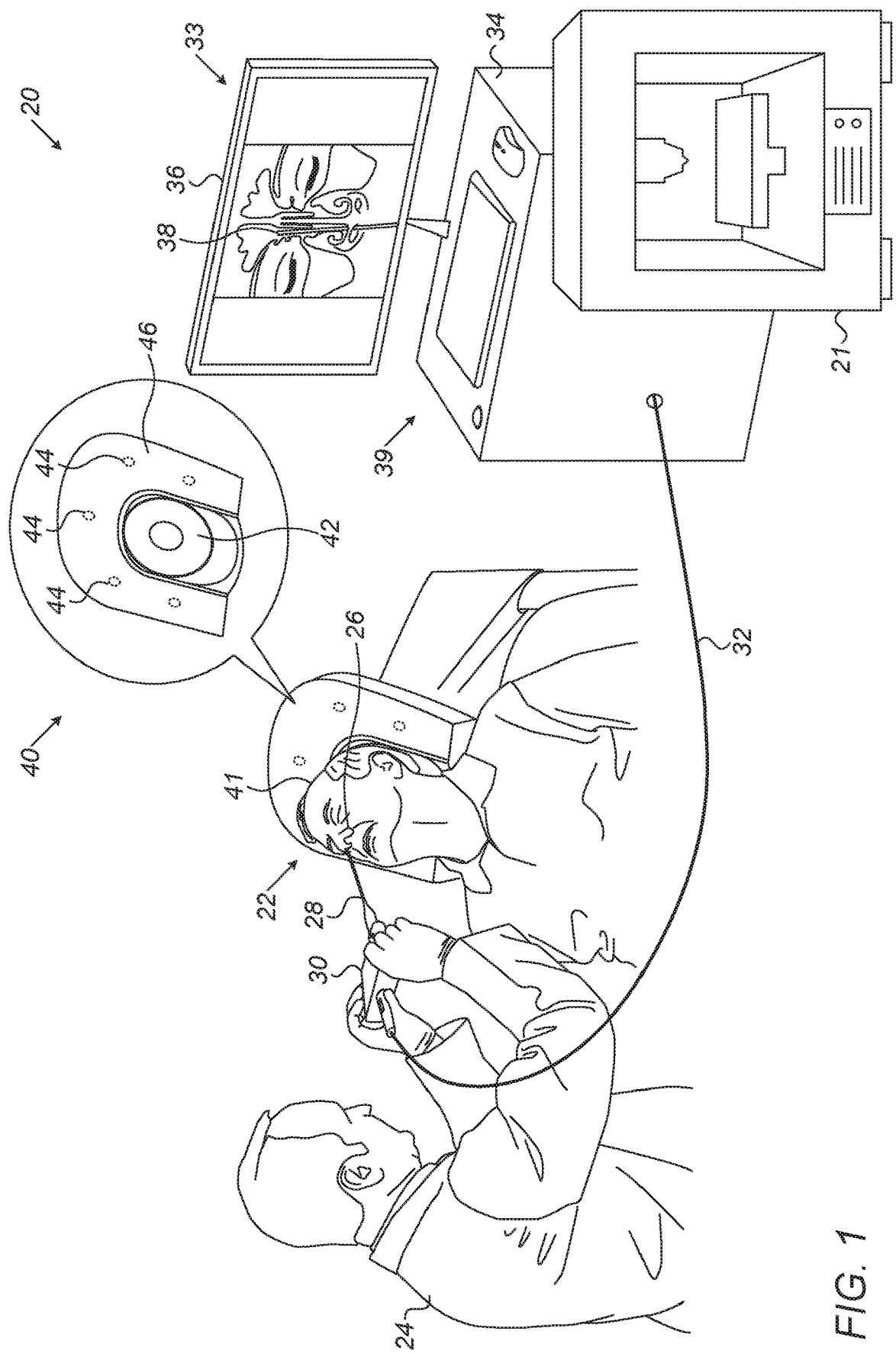
FIG. 1 is a schematic, pictorial illustration of a sinuplasty surgical system, in accordance with an embodiment of the present invention.

Position tracking systems are typically used for navigating catheters, such as suction catheters and guidewires, in image-guided procedures such as sinuplasty. In principle, it is possible to acquire an anatomical image that includes an organ to be treated prior to the medical procedure, and register the image to a coordinate system of the position tracking system. When the image is registered, a position sensor tracked by the system can be displayed at the correct position over the image. A physician may then navigate a medical device having a position sensor thereon using one or more field-generators attached to a frame on a patient's head. Such a solution, however, requires an additional session for adjusting the frame to the specific patient and has limited accuracy because the frame can move relative to the patient's head during the procedure.

Embodiments of the present invention that are described hereinbelow provide improved techniques for registering an anatomical image with the coordinate system of a position-tracking system, using a personalized gripper that is manufactured based on the anatomical image and comprises a position sensor. The shape of the personalized gripper is designed to fit a selected non-movable organ in the head of the specific patient (e.g., a tooth) and therefore has a fixed known location relative to the head during the medical procedure.

Before applying the procedure, an anatomical image of the patient's head is acquired for planning the procedure and for navigating the medical device during the procedure. The embodiments described herein refer mainly to suitable medical device, such as ear-nose-throat (ENT) surgical tools, probes, suction tools, navigation guidewires, shavers, and drillers, however, the disclosed techniques are applicable for any medical instrument used for ENT applications. In some embodiments, the image contains the location in which the gripper is fitted, such as one or more front teeth of the patient. In an embodiment, the shape of the teeth in the image is used to derive instructions for producing a biocompatible personalized gripper that fits the specific patient, using a three-dimensional (3D) printer or any alternative manufacturing technique such as having a bank of grippers for variety of teeth shape.

In an embodiment, the gripper comprises a first position sensor coupled thereto, and the physician fits the gripper on the front teeth. In an alternative embodiment, the physician couples the first position sensor to the gripper and fits the gripper on the front teeth.

In some embodiments, the front teeth to which the gripper was fitted are identified in the image, and the position of the first sensor (in the gripper) is measured using the tracking system so as to register the image with the coordinate system of the position tracking system. Based on the registration, the position of a position sensor measured using the position tracking system can be displayed to the physician, overlaid on the anatomical image. With this kind of display, when the physician inserts an ENT tool having a second position sensor, e.g., at its distal end, into the patient's nose, the distal end is displayed correctly relative to the image. The physician may navigate the ENT tool on the registered anatomical image to a selected location in the patient's head, such as a nasal sinus, so as to carry out the sinuplasty procedure. In an embodiment, the first sensor in the gripper may serve as a reference position so that the second sensor is displayed accurately over the image even when the patient moves his/her head during the procedure.

The disclosed techniques enable automatic registration of the anatomical image to the position tracking system prior to the sinuplasty procedure, thereby eliminating the need for manual registration by the physician during the sinuplasty procedure. Furthermore, the accurate fixation of the gripper to the teeth reduces the need to repeat the registration, for example, when the patient's head moves.

The proposed techniques enable the physician to navigate the ENT tool to the nasal sinus accurately without navigation-related delays, thus shortening the sinuplasty procedure. Furthermore, the disclosed techniques may save time, cost and effort because the patient does not have to attend the additional session for adjusting the frame as described above.

System Description

FIG. 1 is a schematic pictorial illustration of a sinuplasty procedure using a sinuplasty surgical system 20, in accordance with an embodiment of the present invention. System 20 comprises an ear-nose-throat (ENT) tool 28, which a physician 24 inserts into a nose 26 of a patient 22 so as to treat an ENT disease, such as infection in one or more sinuses of patient 22. In some embodiments, tool 28 may comprise a suction catheter, which is configured to draw infected tissue from at least one of the sinuses. In other embodiments, tool 28 may comprise a guidewire, which is configured to guide any suitable medical device into the sinuses of patient 22. Tool 28 further comprises a proximal end 30, configured to control a distal end 38 of the tool.

In an embodiment, system 20 further comprises a magnetic position tracking system, which is configured to track the position of one or more position sensors in the head of patient 22. The magnetic position tracking system comprises magnetic field-generators 44 and one or more position sensors. The position sensors generate position signals in response to the sensed external magnetic fields from the field generators, thereby enabling a processor 34 to map the position of each sensor as will be described below.

This method of position sensing is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 2003/0120150 A1, issued as U.S. Pat. No. 7,729,742 on Jun. 1, 2010, and 2004/0068178 A1, now abandoned, whose disclosures are all incorporated herein by reference.

System 20 further comprises a location pad 40, which comprises field-generators 44 fixed on a frame 46. In the exemplary configuration shown in FIG. 1, pad 40 comprises five field-generators 44 but may comprise any other suitable number of generators 44. Pad 40 further comprises a pillow 42 placed under a head 41 of patient 22, such that generators 44 are located at fixed, known positions external to the patient.

In an alternative embodiment, system 20 comprises an optical position tracking system (not shown), which is configured to track the position of one or more position sensors, such as optical markers, in the head of patient 22. In one example embodiment, the optical position tracking system comprises one or more optical markers mounted on ENT tool 28, as well as on a personalized gripper shown in FIG. 2 below. The optical position tracking system further comprises one or cameras, which are configured to capture one or more images capturing the optical markers on tool 28 and on the gripper. Processor 34 is configured to map the position of each sensor so as to estimate the position and orientation of the distal tip (shown in FIG. 2 below) of tool 28 in the coordinate system of the optical position tracking system.

System 20 further comprises a console 33, which comprises processor 34, typically a general-purpose computer, with suitable front end and interface circuits for receiving signals from tool 28 having a magnetic sensor attached thereon (shown in FIG. 2 below), via a cable 32, and for controlling other components of system 20 described herein. Processor 34 is further configured to derive one or more instruction files for use by a three-dimensional (3D) printer 21, typically located at a production site, away from the location of system 20. The instruction files are derived from one or more anatomical images of head 41, as will be described in detail in FIG. 2 below. Console 33 further comprises input devices 39 and a user display 36, which is configured to display the data (e.g., images) received from processor 34 or inputs inserted by a user (e.g., physician 24).

Console 33 comprises a driver circuit (not shown), which is configured to drive field-generators 44 with suitable signals so as to generate magnetic fields in a predefined working volume around head 41.

FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description.

Processor 34 may be programmed in software to carry out the functions that are used by the system, and to store data in a memory (not shown) to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Figure 2:
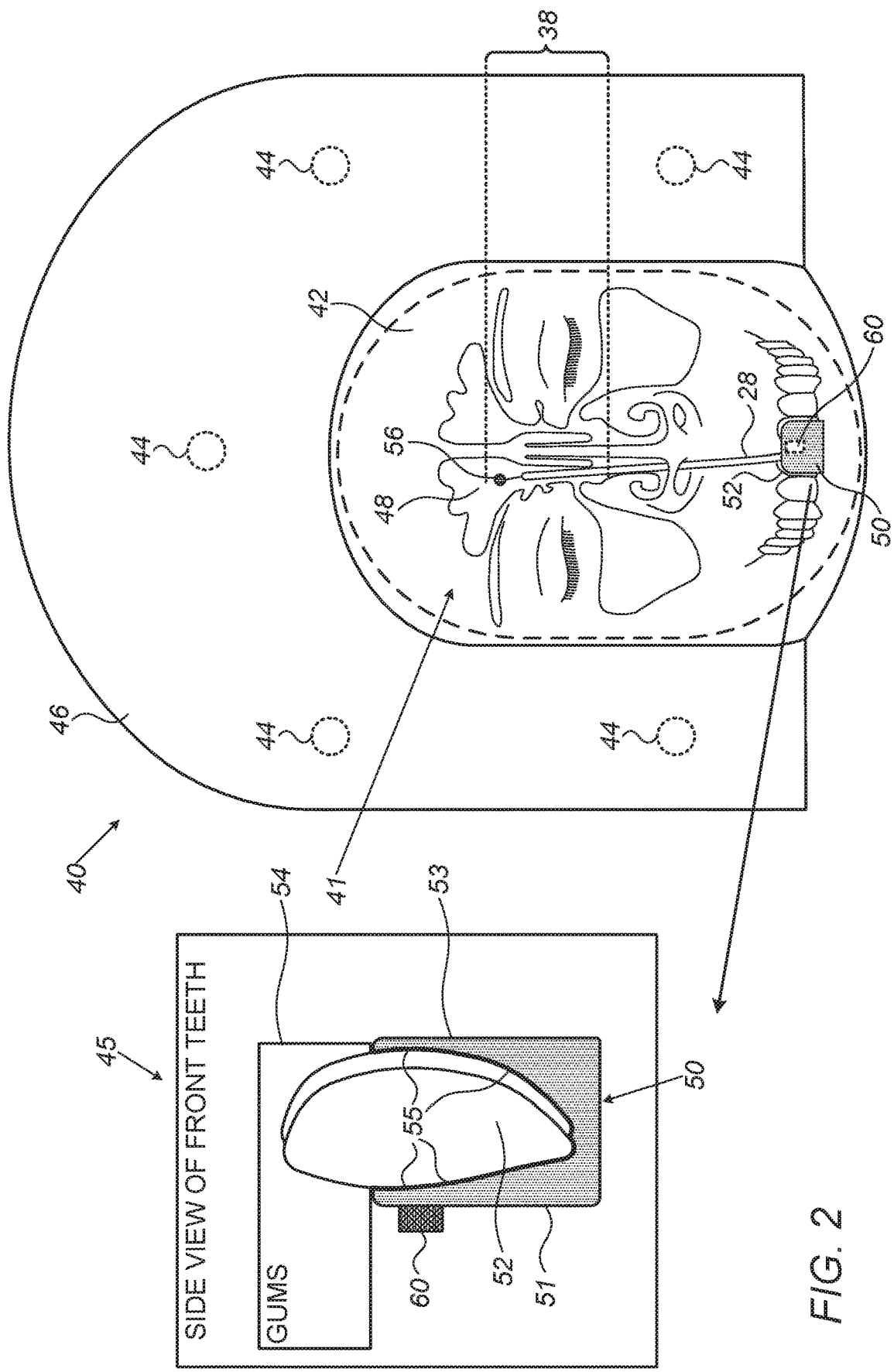
FIG. 2 is a schematic, pictorial illustration of elements of a sinuplasty surgical system, in accordance with an embodiment of the present invention.

FIG. 2 is a schematic, pictorial illustration of elements of sinuplasty surgical system 20, in accordance with an embodiment of the present invention. In an embodiment, prior to the sinuplasty procedure, physician 24 may acquire one or more anatomical images of head 41, using any suitable imaging modality, such as computerized tomography (CT), cone beam computed tomography (CBCT), or magnetic resonance imaging (MRI). The image may be used for planning the procedure beforehand, as well as for navigating ENT tool 28 into a nasal sinus 48 during the procedure.

In some embodiments, the anatomical image may also be used for deriving instructions for producing a personalized gripper 50 that is shaped to fit front teeth 52 of the specific patient 22. In the present context and in the claims, the term "personalized gripper" refers to a gripper intended to fit a specific organ of a specific patient. The specific organ that can verify accurate fitting of the sensor (e.g., teeth 52) typically differs in shape from one patient to another so that the personalized gripper fits, for example, teeth 52 of specific patient 22, but generally not the teeth of any other patient. In an embodiment, processor 34 may be configured to derive one or more instruction files for producing gripper 50 using printer 21.

In alternative embodiments, gripper 50 may be produced using any suitable technique, such as techniques for producing molds for dental prostheses. In yet alternative embodiments, a set of grippers may be pre-produced for a specific organ (e.g., front teeth), using printer 21 or any other suitable production technique. Each gripper of the set may be shaped to fit a different group of patients, for example each group having similar size and shape of the front teeth, so that the set may cover a wide variety of groups of patients. In an embodiment, processor 34 may use the anatomical image to derive the shape of the front teeth of a specific patient, and guide physician 24 to select from the set the most suitable gripper for the specific patient. A gripper that is selected for a particular patient from a set of predefined grippers is also regarded herein as a personalized gripper.

Reference is now made to an inset 45, which is a side-view of the upper front jaw of patient 22. As explained above and as can be seen in the figure, an internal surface 55 of the gripper 50 is personally shaped to fit the external surface of gums 54 and one or more front teeth 52 of the specific patient.

In an embodiment, prior to the sinuplasty procedure, physician 24 may couple (e.g., using a dental glue) a magnetic position sensor 60, for example, to an internal wall 51 of gripper 50, and then fit gripper 50 on gum 54 around front teeth 52. The term "internal wall" refers to a wall of gripper 50 facing the inner mouth of patient 22. Alternatively, physician 24 may couple sensor 60 at any other suitable location on gripper 50. In an alternative embodiment, sensor 60 may be already embedded in gripper 50 so that physician 24 may only fit the gripper on teeth 52.

In some embodiments, gripper 50 may comprise a personalized-shaped trench that allows fitting an internal surface 55 of gripper 50 to the external surfaces of gums 54 and teeth 52, as shown in inset 45. In alternative embodiments, gripper 50 may have any suitable 3D or even two-dimensional (2D) shape that allows fitting sensor 60 stiffly to any suitable organ or tissue in head 41.

System 20 further comprises a magnetic position sensor 56 attached to the tip of distal end 38, which is inserted into nasal sinus 48 during the sinuplasty procedure as described in detail in FIG. 4 below. The position of sensor 56 is typically measured using the magnetic position tracking system, as described in FIG. 1 above.

In other embodiments, gripper 50 may comprise a registration groove (not shown) formed, for example, in an external wall 53 of gripper 50. The registration groove is located at a fixed coordinate offset relative to sensor 60. Before the sinuplasty procedure, physician 24 may insert the distal tip of tool 28 (which comprises position sensor 56) into the registration groove so as to calibrate the position of sensor 56 in a coordinate system of the magnetic position tracking system. The calibration is carried out by assigning to sensor 56 initial coordinates that are in a known offset relative to the coordinates of the gripper sensor as the groove. In an alternative embodiment, system 20 may comprise an optical-based positioning system for calibrating the position of an optical sensor (instead of sensor 56) when the tip is inserted into the groove.

In alternative embodiments, gripper 50 may be formed to fit any other suitable organ in head 41, for example, a bite bar for the upper and lower jaws, a nose gripper, or a head clamp. In an embodiment, the shape of the organ in the anatomical image, to which the gripper is to be fitted, may be used to derive instructions for producing the personalized gripper. The anatomical image should typically include the entire organ in question. In an example embodiment, the anatomical image may comprise at least part of the upper and lower jaws of the specific patient. These jaw parts may be used to derive the instructions for producing a personalized bite bar or a teeth gripper.

In another embodiment, the anatomical image may capture at least part of a cranium of head 41 so as to derive instructions to produce the personalized head clamp that fits the specific part of the cranium of patient 22. In yet another embodiment, the anatomical image may capture at least part of nose 26 so as to derive instructions to produce the nose gripper.

Figure 3:
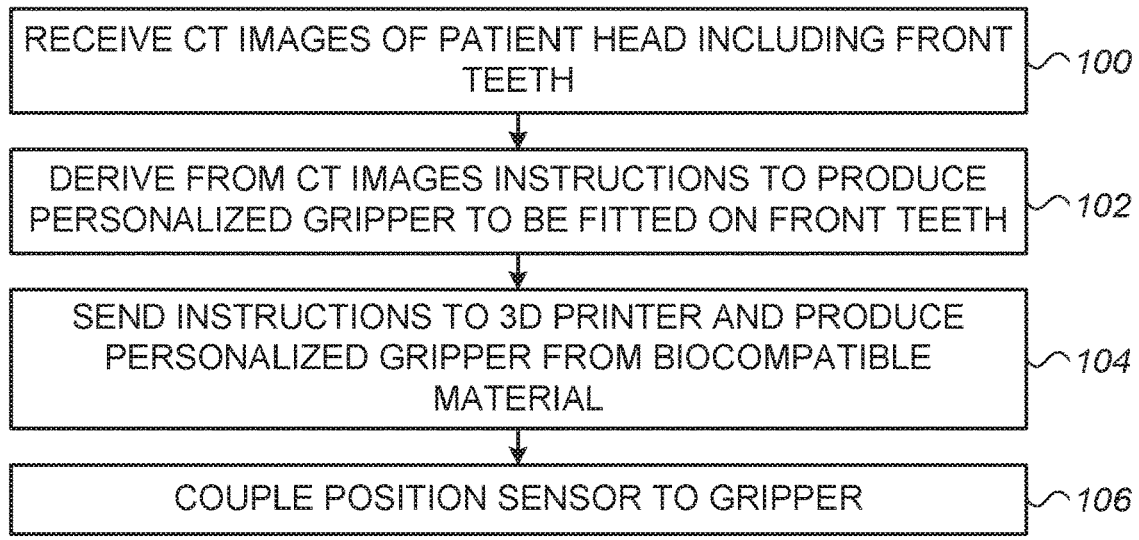
FIG. 3 is a flow chart that schematically illustrates a method for producing a personalized gripper, in accordance with an embodiment of the present invention.

FIG. 3 is a flow chart that schematically illustrates a method for producing personalized gripper 50, in accordance with an embodiment of the present invention. The method begins with processor 34 receiving one or more CT images capturing at least part of head 41, at a CT imaging step 100. The CT images in this example capture at least teeth 52, which are selected by physician 22 for fitting gripper 50. In the present example, based on the CT images, the method generates instructions for producing gripper 50, which is personalized to teeth 52 of specific patient 22.

At an instruction deriving step 102, processor 34 analyzes the CT images to identify in the images the shape of teeth 52, which is specific to patient 22. Processor 34 derives, based on the identified shape of teeth 52, one or more instruction files that comprises machine instructions producing gripper 50.

At a gripper formation step 104, system 20 may send the instruction files to the 3D printer for producing personalized gripper 50, typically from biocompatible materials. At a position sensor coupling step 106, an operator (e.g., physician 24, or a manufacturing technician) couples sensor 60 to gripper 50 as depicted in FIG. 2 above.

Figure 4:
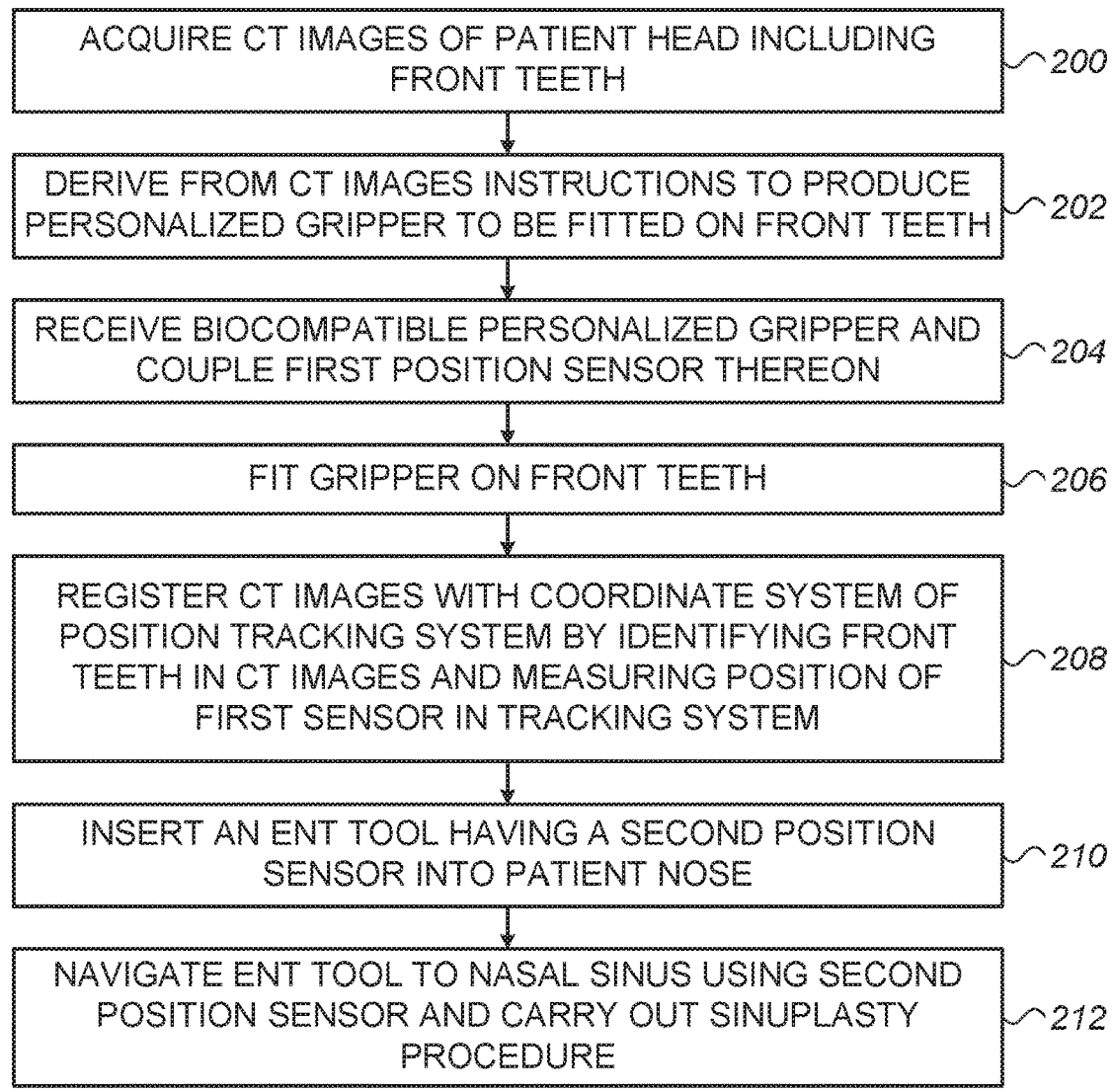
FIG. 4 is a flow chart that schematically illustrates a method for carrying out a sinuplasty procedure using a personalized gripper, in accordance with an embodiment of the present invention.

FIG. 4 is a flow chart that schematically illustrates a method for carrying out a sinuplasty procedure using personalized gripper 50, in accordance with an embodiment of the present invention. The method begins with acquiring one or more CT images of at least part of head 41 (e.g., using an external CT imager), and providing the CT images to processor 34, at an imaging step 200. The CT images capture at least teeth 52, which is selected in advance by physician 22 for fitting gripper 50.

At an instruction deriving step 202, processor 34 derives from the CT image, the instruction files for producing gripper 50, as described at instruction deriving step 102 above. At a sensor coupling step 204, physician 22 couples position sensor 60 to personalized gripper 50 that was produced at step 202. In alternative embodiments, gripper 50 already comprises sensor 60 embedded therein at production.

At a gripper fitting step 206, physician 22 fits internal surface 55 of gripper 50 on the external surfaces of gums 54 and teeth 52, as shown in inset 45. At a registration step 208, processor 34 registers the one or more CT images with the coordinate system of the magnetic position tracking system by identifying front teeth 52 in the CT image and measuring the position of sensor 60 (that is coupled to gripper 50 and therefore has a fixed location relative to teeth 52) in the coordinate system of the position tracking system. Note that after the registration, the position of sensor 60 is anchored to teeth 52 in the coordinate system, and therefore, also in the CT images during the procedure, even when moving the head of patient 22.

At an ENT tool insertion step 210, physician inserts tool 28 into nose 26 of patient 22 so as to carry out the sinuplasty procedure. Sensor 56, which is attached at the distal tip of tool 28 allows physician 24 to track the position of distal end 38 using the magnetic position tracking system. At a navigation step 212, physician 24 navigates distal end 38 into nasal sinus 48 using position sensor 56 whose measured position is displayed overlaid on the CT image.

In some embodiments, by continuously tracking the position of sensor 60 relative to sensor 56, processor 34 is configured to dynamically maintain the registration of the CT image with the position tracking system even when patient 22 moves his/her head. Furthermore, processor 34 may continuously display the position of sensors 56 and 60 on the CT image displayed of user display 36, thus, assisting physician 24 to carry out the sinuplasty procedure.

In other embodiments, the proposed techniques may be used, mutatis mutandis, in various other types of surgical, diagnostic and therapeutic procedures. For example, a neuro-surgeon may use gripper 50 on teeth 52 for tracking one or more ENT tools in a neural-system of patient 22, such as patient's brain or spinal cord.

In alternative embodiments, the disclosed technique may be used in any surgical procedure, such as brain surgery, in a spinal cord, by fitting the personalized gripper to a suitable organ or tissue such as one of the spinal vertebras.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:
1. A method, comprising:
(a) acquiring an anatomical image of at least part of a head of a specific patient, wherein the anatomical image captures at least a selected location in the head;
(b) fitting a personalized gripper, which is shaped based on the anatomical image to personally fit one or more teeth of the specific patient at the selected location, the personalized gripper comprising:
(i) a body portion,
(ii) a sensor placement position located on the body portion, wherein the sensor placement position is associated, in an electronic memory of a surgical system, with a first fixed coordinate offset describing the sensor placement position relative to the one or more teeth when the personalized gripper is fit to the one or more teeth, and
(iii) a first position sensor of a position-tracking system positioned at the sensor placement position, wherein the position-tracking system comprises a magnetic position-tracking system, and wherein the first position sensor comprises a magnetic position sensor;

(c) registering the anatomical image with a coordinate system of the position-tracking system, by identifying the selected location in the anatomical image and measuring a first position of the first position sensor using the position-tracking system, wherein registering comprises:
  (i) generating an electromagnetic field around the head of the patient, and
  (ii) receiving signals from the first position sensor in response to the generated electromagnetic field;

(d) calibrating the position-tracking system for a second position sensor using a registration groove on an external wall of the body portion of the personalized gripper, wherein:
  (i) the registration groove is adapted to couple with a portion of a medical device and statically position the medical device relative to the first position sensor,
  (ii) the registration groove is positioned on the external wall based on a second fixed coordinate offset describing the registration groove position relative to the first position sensor, and
  (iii) calibration of the position tracking system for the second position sensor is based on the second fixed coordinate offset; and (e) navigating to one or more locations in the head of the specific patient the medical device that comprises the second position sensor of the position-tracking system, by displaying a second position of the medical device in the head on the registered anatomical image, wherein the second position sensor comprises a second magnetic position sensor, wherein navigating comprises:
  (i) receiving signals from the first position sensor, in response to the generated electromagnetic field, to indicate positioning of the head of the patient,
  (ii) receiving signals from the second position sensor, in response to the generated electromagnetic field, to indicate positioning of the medical device, and
  (iii) displaying the second position of the medical device based upon the indicated positioning of the head of the patient and the indicated positioning of the medical device.

2. The method according to claim 1, wherein acquiring the anatomical image comprises acquiring one or more images using a modality selected from a list consisting of computerized tomography (CT), cone beam computed tomography (CBCT), and magnetic resonance imaging (MRI).

3. The method according to claim 1, wherein navigating the medical device comprises navigating the medical device into a nasal-sinus of the head.

4. The method according to claim 1, wherein navigating the medical device comprises navigating the medical device into a neural-system of the head.

5. The method according to claim 1, wherein the medical device comprises a suction catheter.

6. The method according to claim 1, wherein the medical device comprises a guidewire.

7. A method for producing a gripper, the method comprising:
  (a) receiving an anatomical image of at least part of a head of a specific patient, wherein the anatomical image captures at least a selected location in the head;
  (b) deriving from the anatomical image instructions for producing a personalized gripper that is shaped to personally fit one or more teeth at the selected location;
  (c) producing the personalized gripper based on the instructions and providing a registration groove at a groove position on an external wall of a body portion of the personalized gripper, wherein the registration groove is adapted to couple with a portion of a medical device and statically position the medical device relative to the personalized gripper;
  (d) associating the registration groove, in an electronic memory, with a second fixed coordinate offset describing the groove position relative to a sensor placement position;
  (e) coupling a position sensor to the personalized gripper at the sensor placement position on the body portion of the personalized gripper, wherein the position sensor comprises a magnetic position sensor configured to generate a position-indicative signal in response to an electromagnetic field; and
  (f) associating the position sensor, in the electronic memory of a surgical system, with a first fixed coordinate offset describing the sensor placement position relative to the one or more teeth.

8. The method according to claim 7, wherein receiving the anatomical image comprises receiving one or more images of a modality selected from a list consisting of computerized tomography (CT), cone beam computed tomography (CBCT), and magnetic resonance imaging (MRI).

9. The method according to claim 7, wherein producing the personalized gripper comprises printing the personalized gripper by a three-dimensional (3D) printer in accordance with the instructions.

10. The method according to claim 9, wherein printing the personalized gripper comprises printing the personalized gripper from at least one biocompatible material.

11. The method of claim 7, wherein the instructions for producing the personalized gripper comprise a set of known offsets describing spatial relationships between a plurality of points on the personalized gripper, further comprising:
  (a) determining the first fixed coordinate offset at the time the gripper is produced based on the set of known offsets; and
  (b) determining the second fixed coordinate offset at the time the gripper is produced based on the set of known offsets.

12. An article of manufacture, comprising:
  (a) a personalized gripper body, which is shaped to personally fit one or more teeth at a selected location in a head of a specific patient, based on an anatomical image of at least part of the head of the specific patient; and
  (b) a position sensor coupled to the personalized gripper body at a sensor placement position, wherein the position sensor comprises a magnetic position sensor configured to generate a position-indicative signal in response to an electromagnetic field, and wherein the position sensor is associated, in an electronic memory of a surgical system, with a fixed coordinate offset describing the sensor placement position relative to the one or more teeth;
  wherein:
    (i) the personalized gripper body comprises a groove, which is shaped to fit a distal tip of a catheter,
    (ii) the groove is positioned at a groove position on an external wall of the personalized gripper body, and
    (iii) the groove is associated, in the electronic memory, with a second fixed coordinate offset describing the groove position relative to the sensor placement position.

13. The article of manufacture according to claim 12, wherein the personalized gripper is made of at least one biocompatible material.

14. The article of manufacture according to claim 12, wherein the position sensor is configured to be coupled to the personalized gripper by gluing the position sensor to the personalized gripper.

* * * * *